(12) United States Patent
Okamoto et al.

(10) Patent No.: US 8,455,694 B2
(45) Date of Patent: Jun. 4, 2013

(54) GELLING AGENT AND GEL

(75) Inventors: Hiroaki Okamoto, Ube (JP); Yuki Morita, Ube (JP)

(73) Assignee: National University Corporation Yamaguchi University, Yamaguchi-shi (JP)

( * ) Notice: Subject to any disclaimer, the term of this patent is extended or adjusted under 35 U.S.C. 154(b) by 0 days.

(21) Appl. No.: 13/376,053

(22) PCT Filed: May 31, 2010

(86) PCT No.: PCT/JP2010/059578
§ 371 (c)(1),
(2), (4) Date: Dec. 2, 2011

(87) PCT Pub. No.: WO2010/140699
PCT Pub. Date: Dec. 9, 2010

(65) Prior Publication Data
US 2012/0077885 A1    Mar. 29, 2012

(30) Foreign Application Priority Data
Jun. 4, 2009 (JP) ................................. 2009-134774

(51) Int. Cl.
*C07C 315/00* (2006.01)
*H01M 4/88* (2006.01)

(52) U.S. Cl.
USPC .............................. 568/28; 568/33; 252/182.1

(58) Field of Classification Search
USPC .................................... 568/28, 33; 252/182.1
See application file for complete search history.

(56) References Cited

U.S. PATENT DOCUMENTS

2009/0090891 A1 * 4/2009 Okamoto et al. .......... 252/182.1

FOREIGN PATENT DOCUMENTS

| JP | 2007-191626 A | 8/2007 |
|---|---|---|
| JP | 2007-191627 A | 8/2007 |
| JP | 2007-191661 A | 8/2007 |
| WO | WO 2007/083843 A1 | 7/2007 |
| WO | WO 2007083843 A1 * | 7/2007 |
| WO | WO 2009/078268 A1 | 6/2009 |
| WO | WO 2009078268 A1 * | 6/2009 |

OTHER PUBLICATIONS

Iuchi et al., 214th ECS Meeting, Abstract #96 published on Oct. 13, 2008.*
International Search Report issued in PCT/JP2010/059578 dated Sep. 7, 2010.

* cited by examiner

*Primary Examiner* — Jeffrey S. Lundgren
*Assistant Examiner* — Michael Schmitt
(74) *Attorney, Agent, or Firm* — Birch, Stewart, Kolasch & Birch, LLP

(57) ABSTRACT

A compound represented by the following formula (1) is provided as a gelling agent for gelatinizing a liquid organic compound:

$$C_nF_{2n+1}R^1-\overset{O}{\underset{O}{\overset{\|}{S}}}-Z^1-OR^2O-Z^2-\overset{O}{\underset{O}{\overset{\|}{S}}}-R^3C_mF_{2m+1} \quad (1)$$

wherein n and m are each independently an integer of 2 to 18, $R^1$ and $R^3$ are each independently a single bond or a branched or linear alkylene group having 1 to 6 carbon atoms, $R^2$ is a branched or linear alkylene group having 3 to 18 carbon atoms, and $Z^1$ and $Z^2$ are each independently a phenylene group or a biphenylene group.

2 Claims, 13 Drawing Sheets

GELLING AGENT AND GEL

TECHNICAL FIELD

The present invention relates to a gelling agent for gelatinizing or thickening an organic compound and to a gel.

BACKGROUND ART

Heretofore, in various industrial fields, gelling agents have been used to solidify a liquid substance, that is, jellify or thicken it. For example, they have been used to control the fluidity of an adhesive, coating composition, printing ink or cosmetic, to provide thixotropy, to collect oil outflowing into the sea and to dispose of cooking oil for domestic use and for other purposes in the food manufacturing industry and the medical field. Out of these, gelling agents which solidify water include collagen, gelatin, Japan agar, agar (carrageenan) andpectin, and there are other gelling agents for solidifying organic substances, especially hydrocarbons, alcohols, ketones, esters, other organic solvents and solutions containing any one of them as the main ingredient.

Out of these, gelling agents for solidifying an organic solution include low-molecular weight or high-molecular weight organic compounds. As gelling agents which are low-molecular weight organic compounds, there are known low-molecular weight organic compounds having a hydrogen bonding functional group such as amino group, imide group or urea group in the molecule. As gelling agents which are high-molecular weight organic compounds, there are known polyvinyl alcohol/polyethylene/elastomers, urea resin and polyolefin unwoven fabrics which introduce an oil in the molecule entangled with a high-molecular weight polymer having lipophilic nature to swell it but keep their solid state.

Conventional gelling agents for solidifying an organic solution must be generally used in large quantities, for example, about 5 to 10% based on the solution or tends to change into sol to return to a liquid state at a relatively low temperature, for example, 30 to 40° C. Therefore, it has been desired to improve these disadvantages.

Use of a large amount of a gelling agent for gelatinization is not only economically disadvantageous but also increases the amount of foreign matter contained in a solvent to be gelatinized. When the gelatinized solvent is used, the influence of the gelling agent as an impurity cannot be ignored.

When the upper limit of the gelation temperature is low, the gelling agent may not keep its shape or fluidize to cause a leak due to a small increase in temperature.

Then, the development of a gelling agent which can keep a gel state with a small amount and at a relatively high temperature has been desired.

The inventors of the present invention aimed to develop a gelling agent capable of keeping a gel state even at a relatively high temperature even when it is used in a small amount and already proposed ethers, thioethers and sulfones having a specific structure with a perfluoroalkyl group and a hydrocarbon group (refer to JP-A 2007-191661, JP-A 2007-191627, JP-A 2007-191626 and the pamphlet of International Laid-open 2009/078268).

These low-molecular weight organic gelling agents can keep an organic solution in a gel state even when it is used in a relatively small amount or at a relatively high temperature.

DISCLOSURE OF THE INVENTION

The inventors conducted intensive studies to develop a gelling agent which can keep a gel state even when it is used in a small amount or at a high temperature, for example, 50 to 70° C. and accomplished the present invention.

Other objects and advantages of the present invention will become apparent from the following description.

According to the present invention, firstly, the above objects and advantages of the present invention can be attained by a gelling agent which comprises a compound represented by the following formula (1).

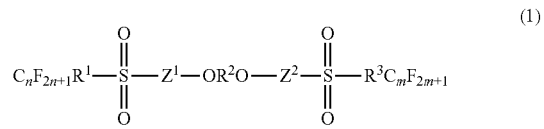

(1)

In the above formula, n and m are each independently an integer of 2 to 18, $R^1$ and $R^3$ are each independently a single bond or a branched or linear alkylene group having 1 to 6 carbon atoms, $R^2$ is a branched or linear alkylene group having 3 to 18 carbon atoms, and $Z^1$ and $Z^2$ are each a phenylene group or a biphenylene group.

According to the present invention, secondly, the above objects and advantages of the present invention are attained by a gel which comprises 0.4 to 5 wt % of the above gelling agent of the present invention and 99.6 to 95 wt % of an organic compound which is liquid at 25° C.

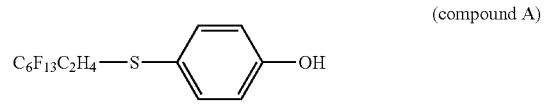

(compound A)

Figure 2:
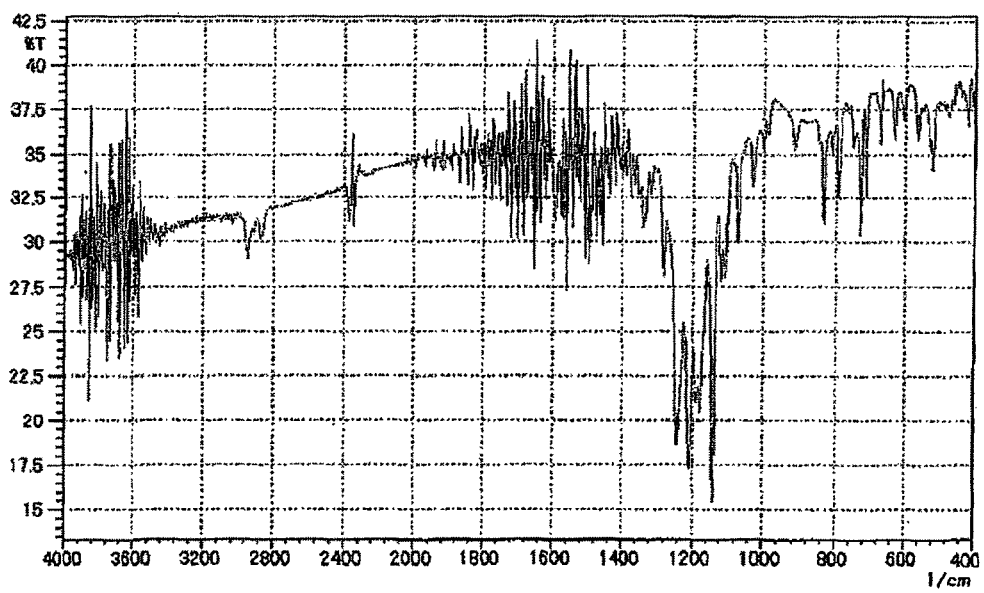

FIG. 2 is an IR spectral diagram of another intermediate 1-5 for the gelling agent of the present invention which is derived from the compound A;

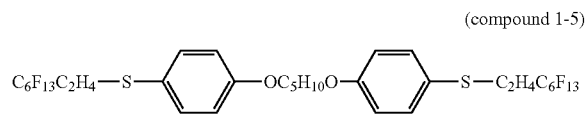

(compound 1-5)

Figure 3:
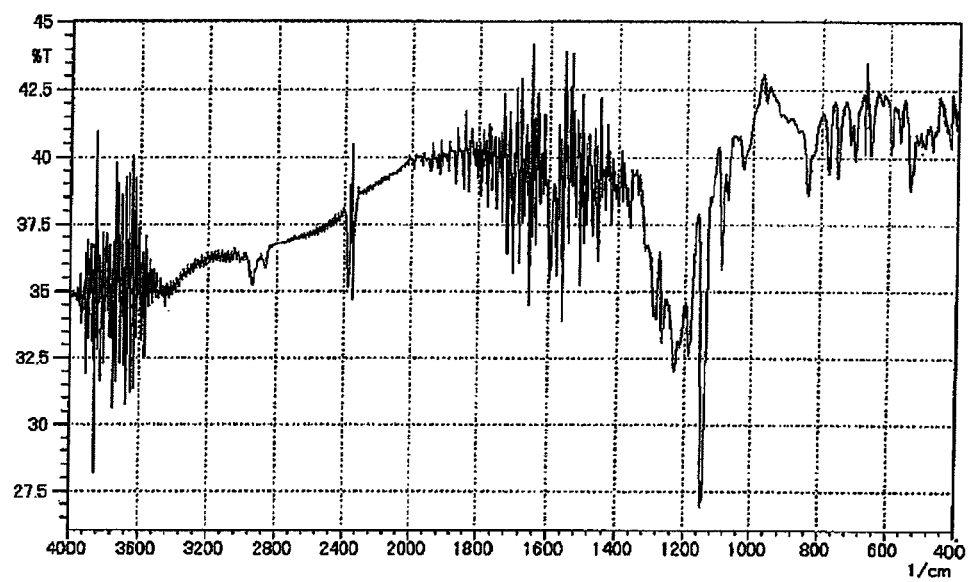

FIG. 3 is an IR spectral diagram of the following compound 2-5 which is a gelling agent of the present invention;

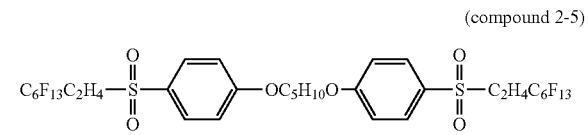

(compound 2-5)

Figure 4:
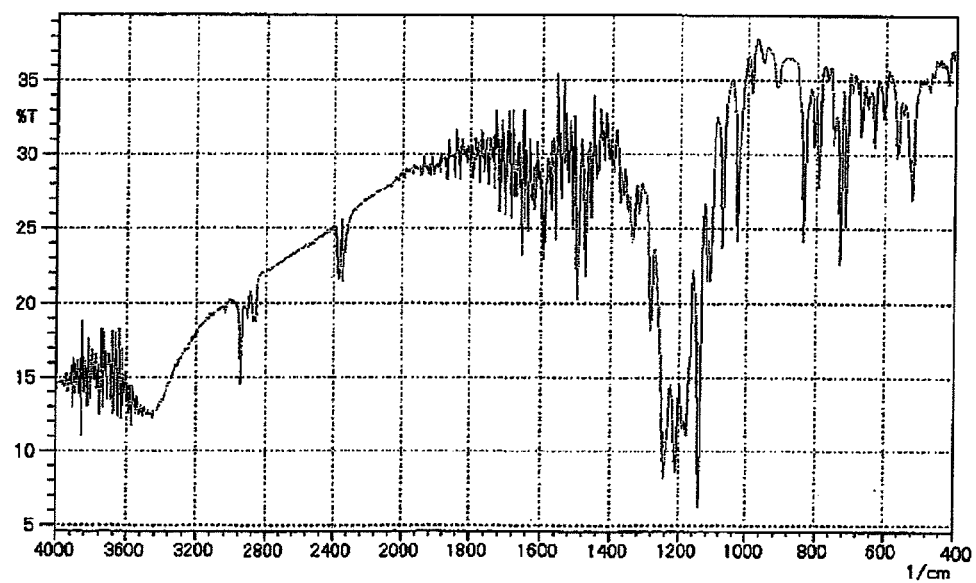

FIG. 4 is an IR spectral diagram of the following compound 1-6 which is still another intermediate for the gelling agent of the present invention;

(compound 1-6)

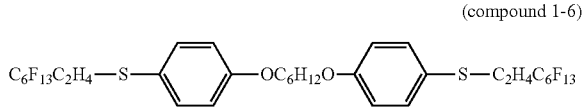

Figure 5:
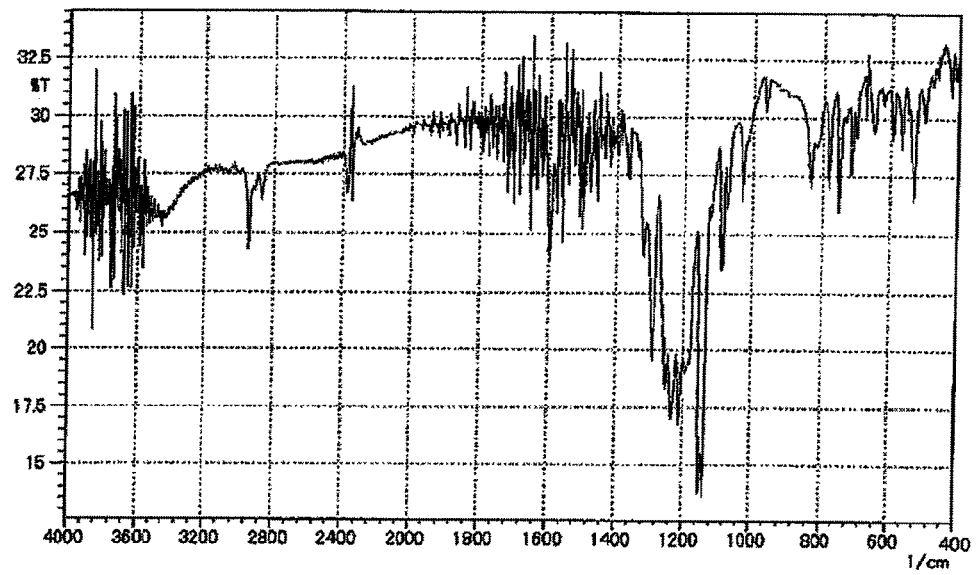

FIG. 5 is an IR spectral diagram of the following compound 2-6 which is another gelling agent of the present invention which is derived from the compound 1-6;

(compound 2-6)

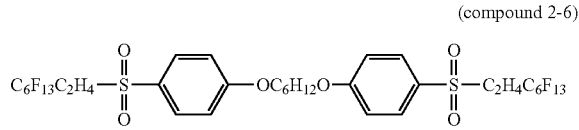

Figure 6:
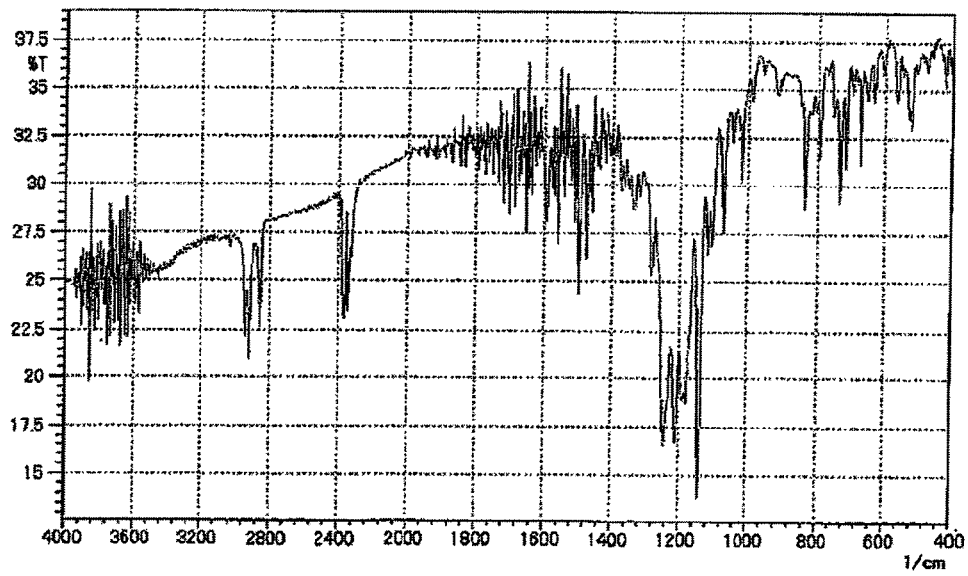

FIG. 6 is an IR spectral diagram of the following compound 1-10 which is a further intermediate for obtaining the gelling agent of the present invention;

(compound 1-10)

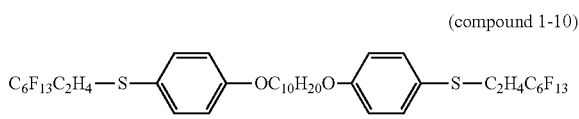

Figure 7:
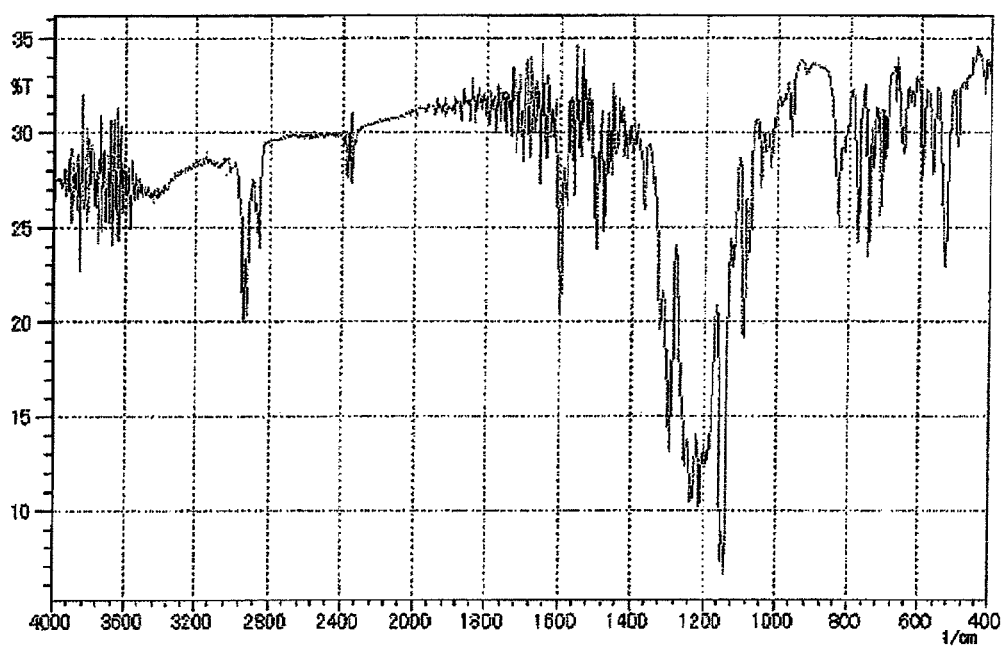

FIG. 7 is an IR spectral diagram of the following compound 2-10 which is still another gelling agent of the present invention which is derived from the compound 1-10;

(compound 2-10)

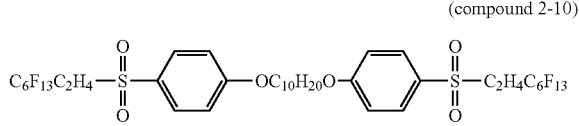

Figure 8:
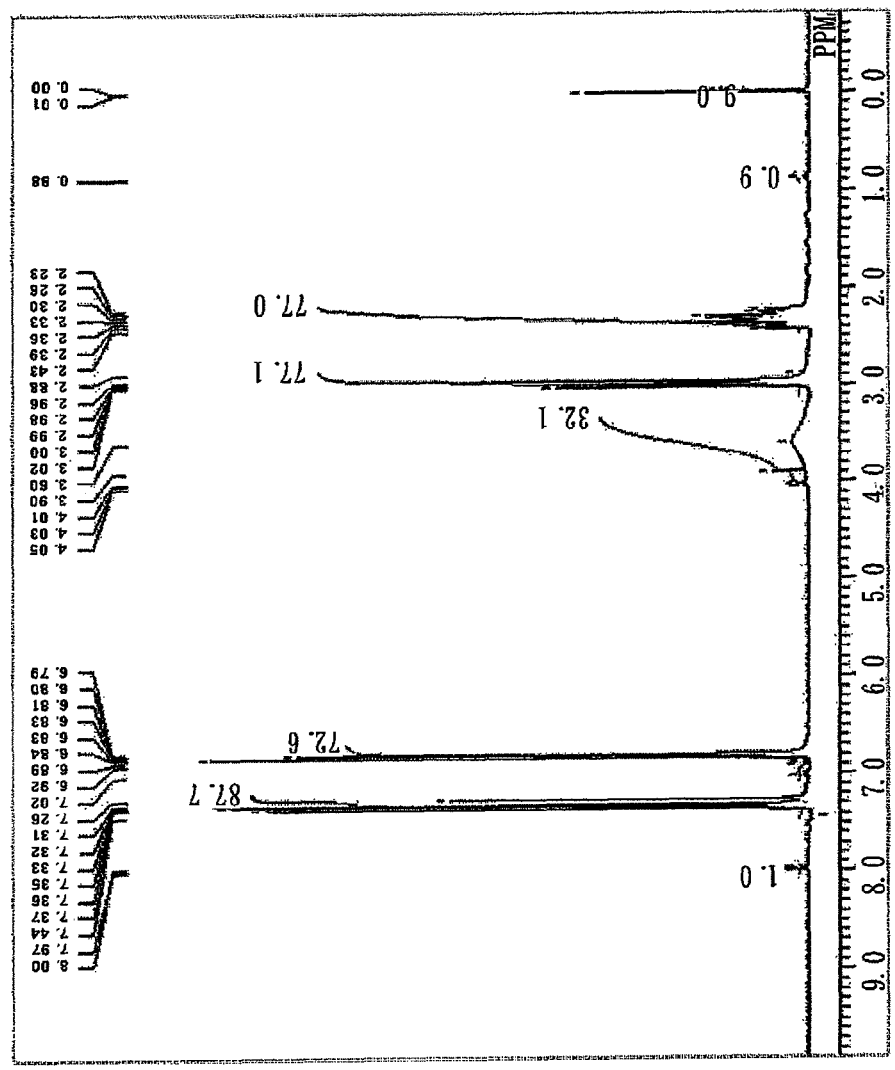
Figure 9:
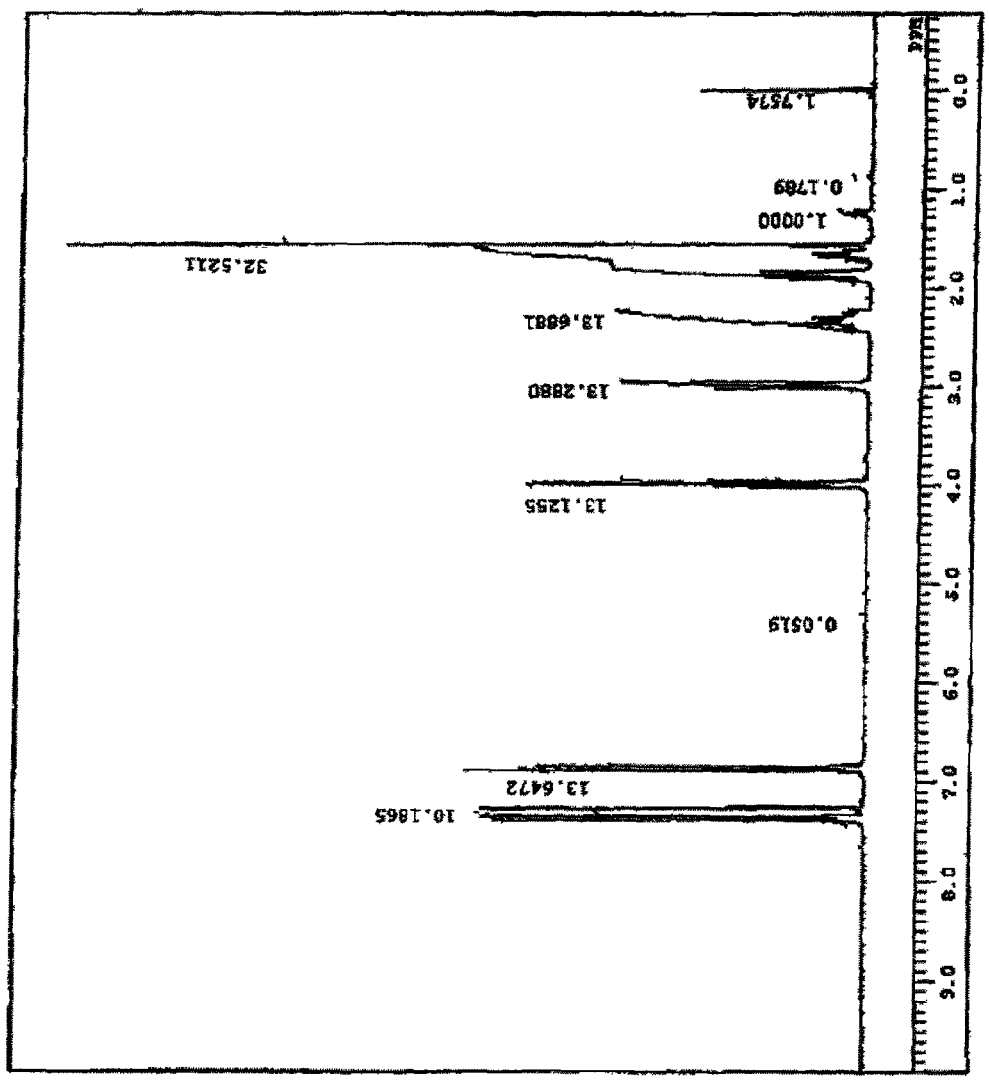
Figure 10:
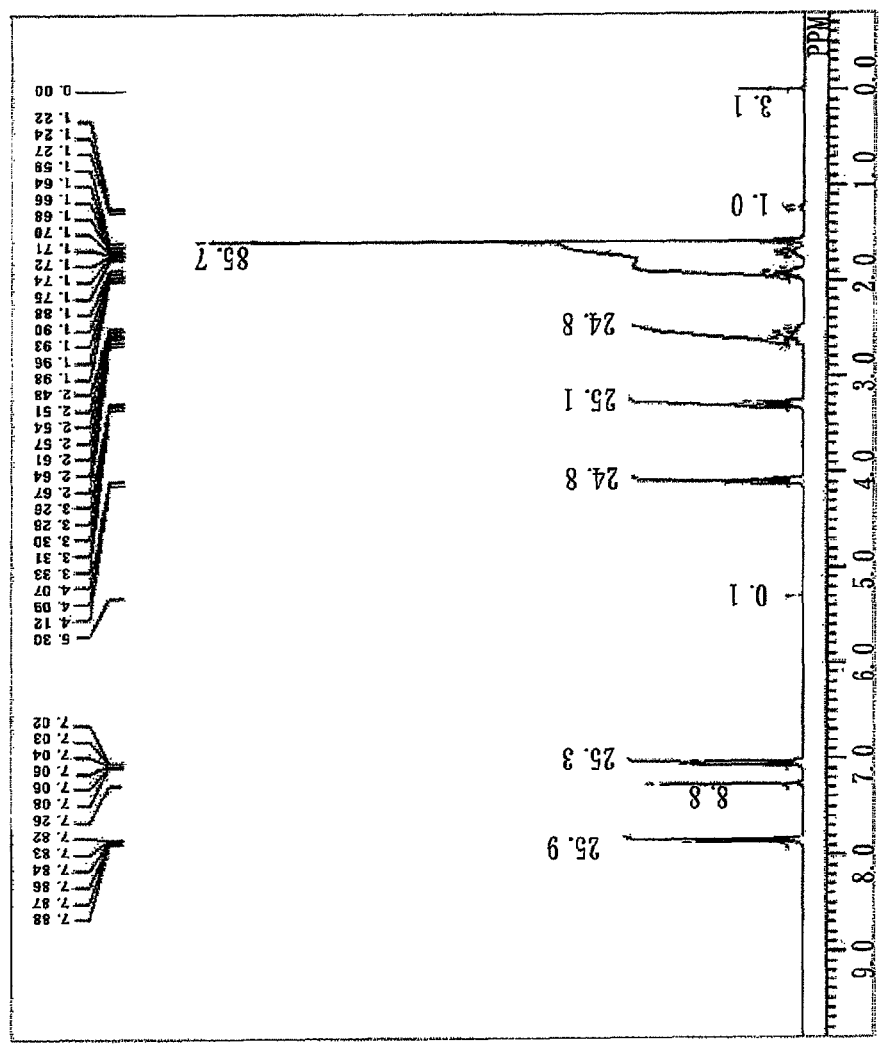
Figure 11:
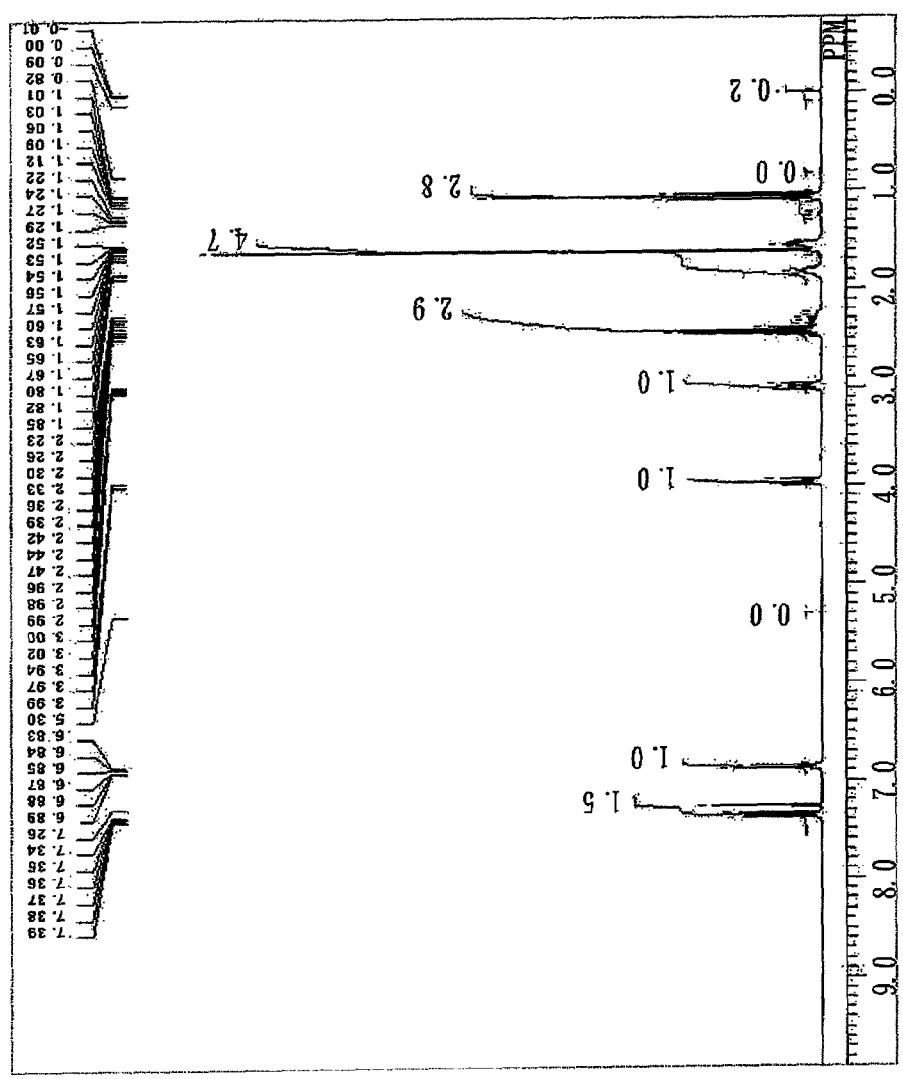
Figure 12:
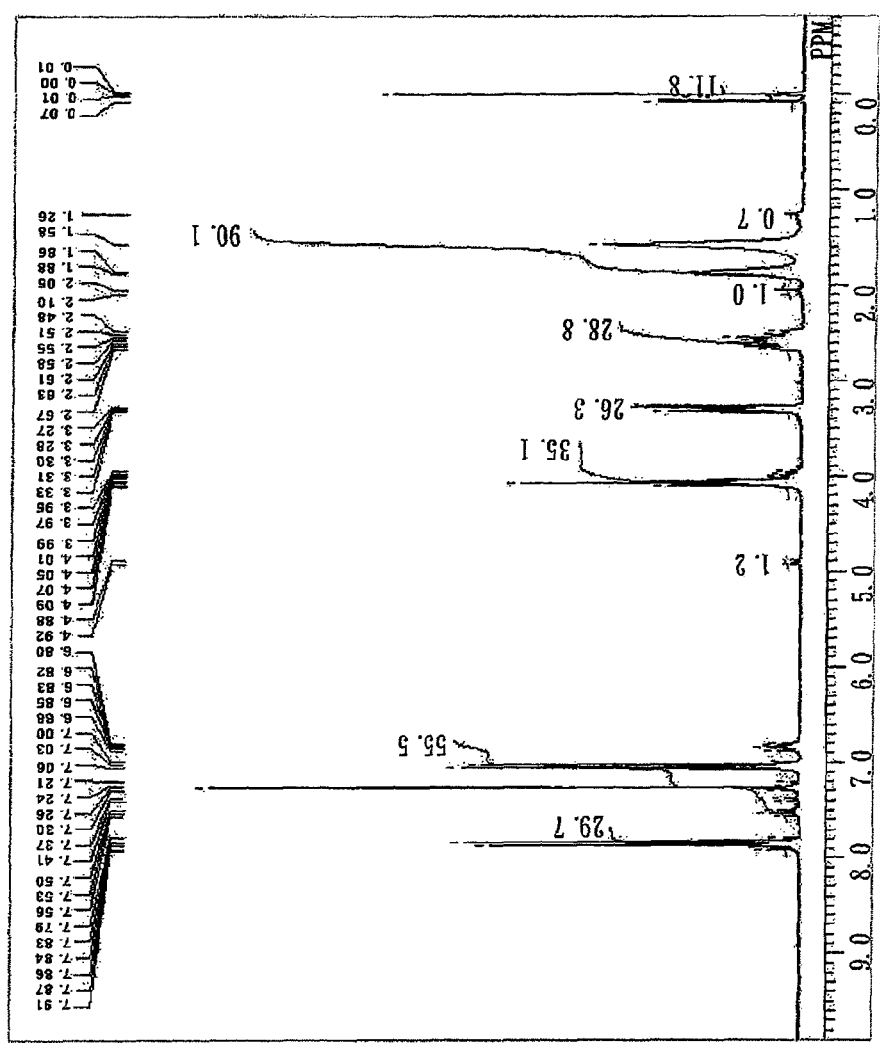
Figure 13:
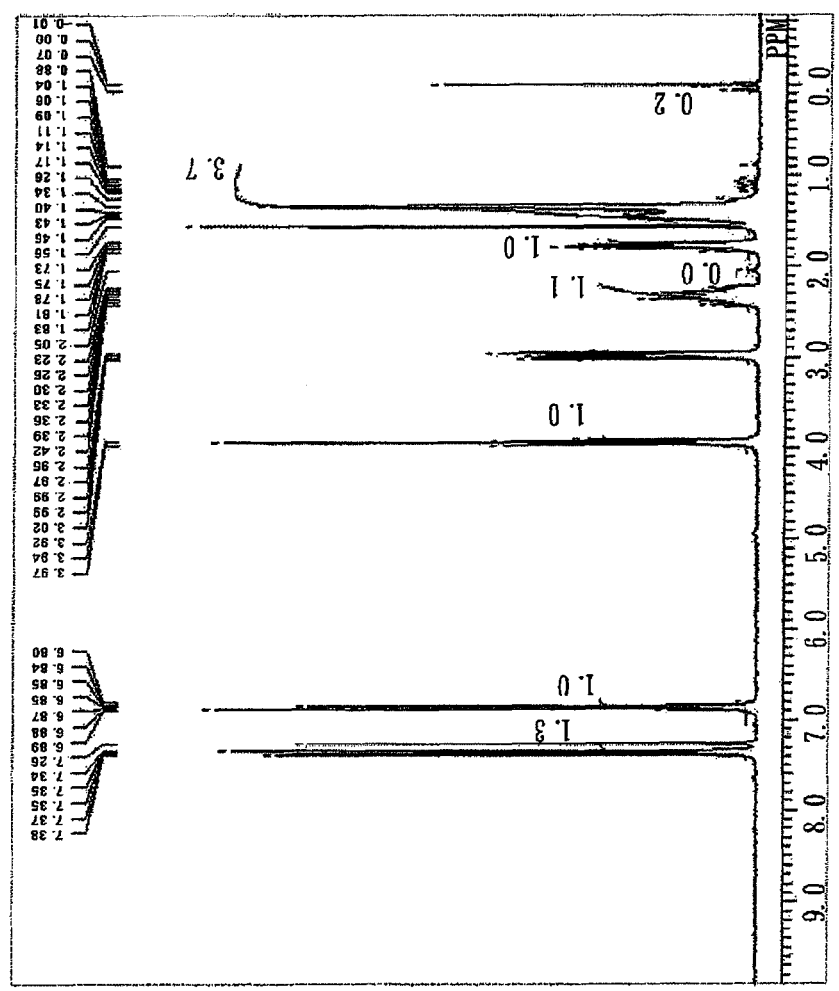
Figure 14:
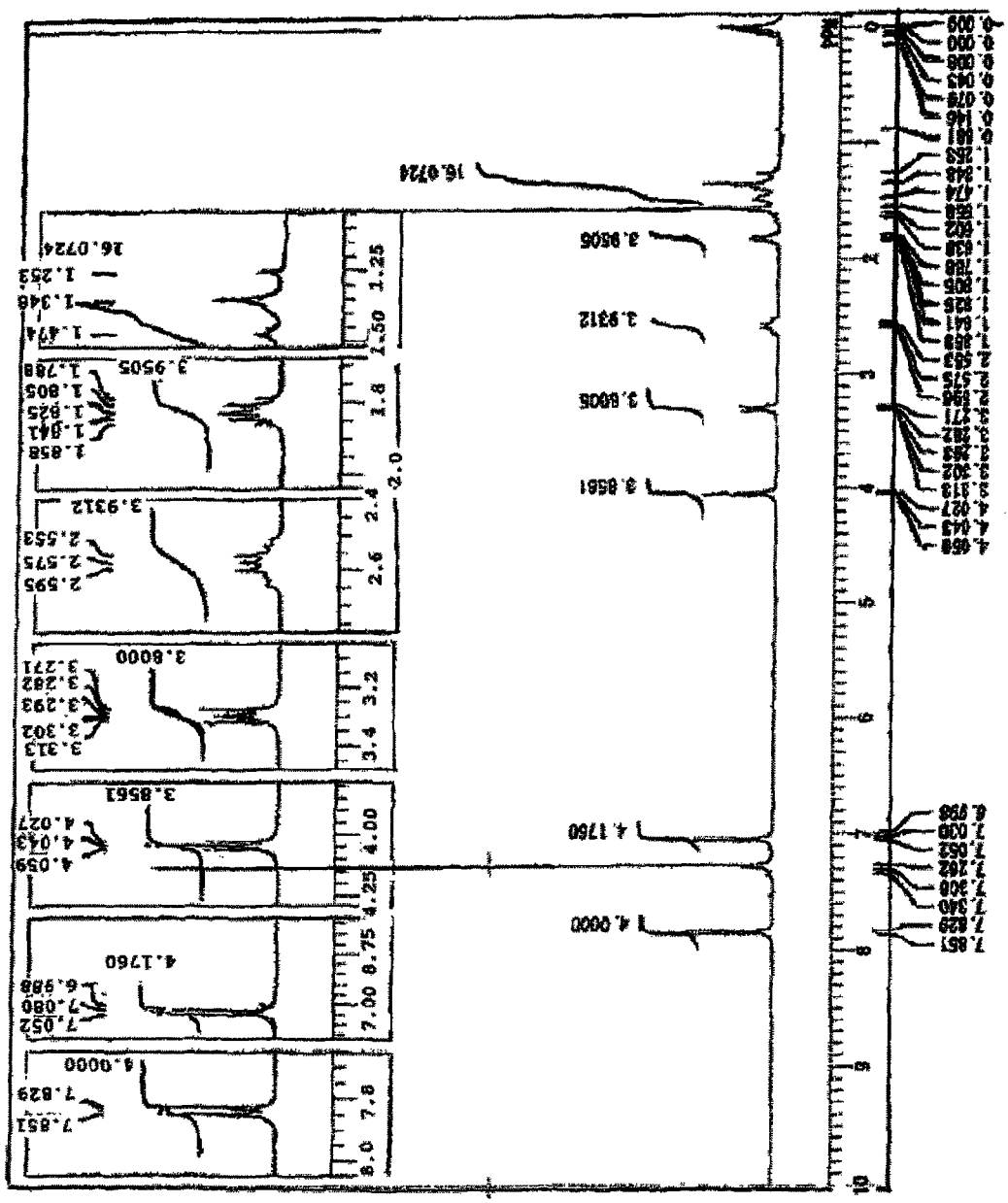
Figure 15:
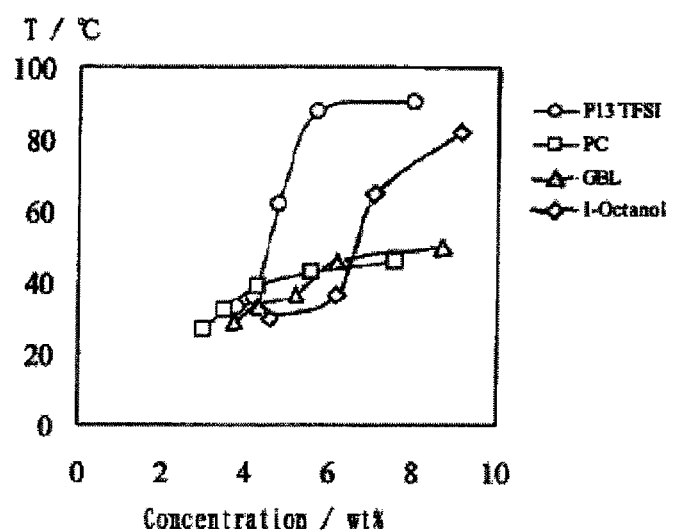
Figure 16:
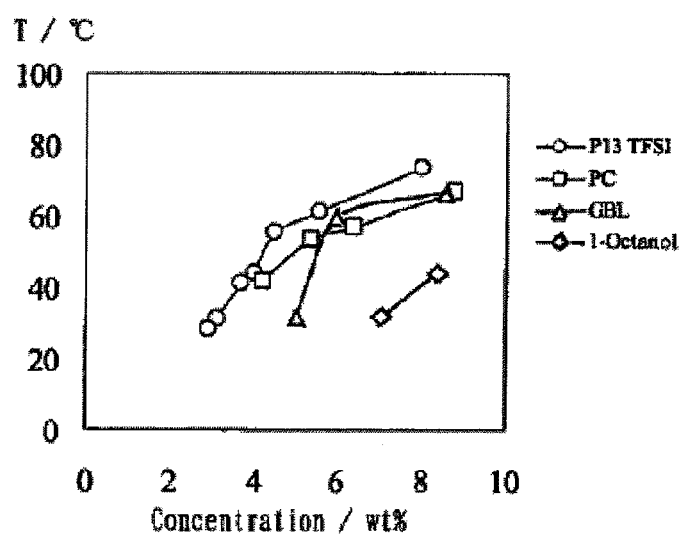
Figure 17:
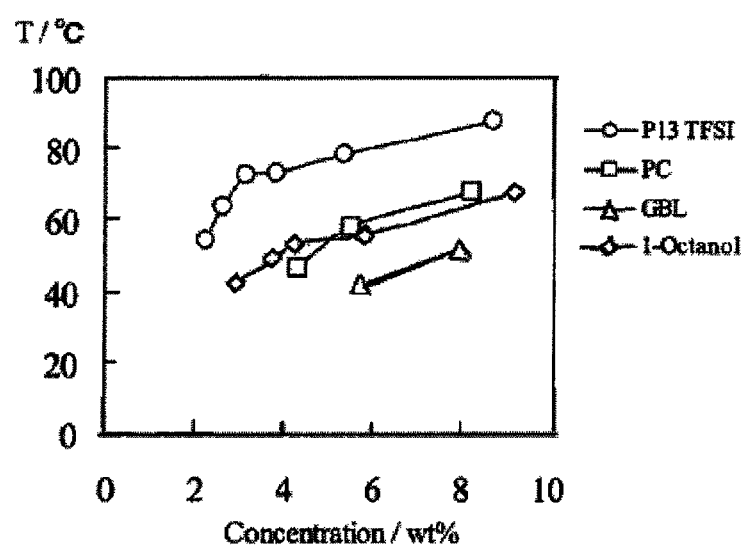

FIG. 8 is an NMR spectral diagram of the compound A;

FIG. 9 is an NMR spectral diagram of the compound 1-5;

FIG. 10 is an NMR spectral diagram of the compound 2-5;

FIG. 11 is an NMR spectral diagram of the compound 1-6;

FIG. 12 is an NMR spectral diagram of the compound 2-6;

FIG. 13 is an NMR spectral diagram of the compound 1-10;

FIG. 14 is an NMR spectral diagram of the compound 2-10;

FIG. 15 is a graph showing the relationship between the concentration of the compound 2-5 and the sol-gel transition temperature;

FIG. 16 is a graph showing the relationship between the concentration of the compound 2-6 and the sol-gel transition temperature; and FIG. 17 is a graph showing the relationship between the concentration of the compound 2-10 and the sol-gel transition temperature.

BEST MODE FOR CARRYING OUT THE INVENTION

The present invention is a gelling agent which comprises a novel compound represented by the following formula (1).

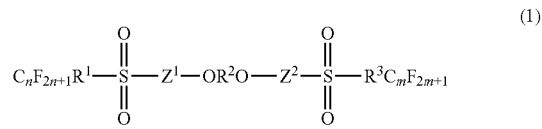

In the above formula, n and m may be the same or different and are each independently an integer of 2 to 18, preferably 4 to 8. When n and m are each larger than 8, synthesis becomes difficult and there arises an environmental concern. When they are smaller than 2, the gelation ability degrades.

$R^1$ and $R^3$ are each independently a single bond or the same or different alkylene groups having 1 to 6 carbon atoms and may be branched or linear. They are preferably ethene groups (—$C_2H_4$—) or propene groups (—$C_2H_6$—).

$R^2$ is a branched or linear alkylene group having 3 to 18 carbon atoms. When the number of carbon atoms is smaller than 3, gelatinization hardly occurs and when the number is larger than 18, gelatinization is carried out but synthesis becomes difficult. $R^2$ is preferably an alkylene group having 4 to 12 carbon atoms.

$Z^1$ and $Z^2$ are each independently a phenylene group or a biphenylene group. The phenylene group and the biphenylene group may have a substituent as the case may be. When they are biphenylene groups, gelatinization tends to occur with a smaller amount of a gelling agent. However, a phenylene group can be advantageously used because an intermediate can be easily acquired.

The characteristic feature of the compound of the gelling agent of the present invention is that it is a relatively long molecule with two ether bonds and 2 sulfone groups. It is assumed that the former in this molecular structure increases the degree of rotation freedom in the compound, provides flexibility to the molecule and produces a loose link between molecules due to the hydrogen bonding property of the sulfone group, thereby forming needle-like molecular masses as seen in a liquid crystal to form aggregates and causing gelatinization by making a liquid organic compound existent between the aggregates.

That is, it is considered that the gelling agent of the present invention has strong potential of a gelatinization mechanism which differs from those of many conventionally known gelling agents.

The gel-sol transition temperature of the gelling agent of the present invention greatly changes according to the amount of the gelling agent and the type of an organic compound to be gelatinized as shown in FIGS. 15 to 17. Therefore, when the gelling agent is actually used by a person skilled in the art, it should be preliminarily tested to determine the gelling agent which is used with a liquid organic compound to be gelatinized and its amount.

Although the manufacturing process of the gelling agent of the present invention is not limited at all, the gelling agent of the present invention can be generally synthesized based on the following scheme.

That is, a compound (II) is synthesized from the following compound (I) which is commercially available.

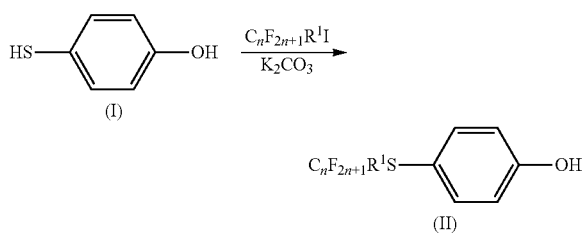

(in the above reaction formula, $R^1$ and n are as defined in the above formula (1).)

As a matter of course, 4-hydroxy-4'-mercaptobiphenyl may be used in place of the compound (I). The reaction of the compound (I) is shown below. Then, the compound (II) is dimerized as follows to obtain a compound (III).

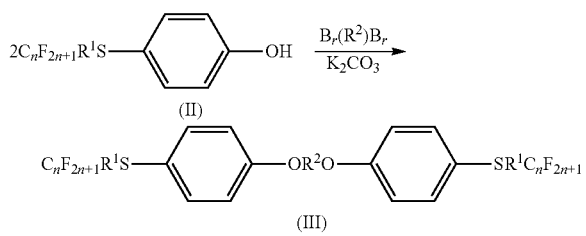

(In the above reaction formula, $R^1$, $R^2$ and n are as defined in the above formula (1).)

In this case, the number of carbon atoms of the right and left perfluoroalkyl groups may be changed from n to m and $R^1$ may be changed to $R^2$ optionally in place of the compound (II). When two different compounds (II) are used for dimerization, these compounds do not always react with each other in a ratio of 1:1. Therefore, it is preferred that the same type of compounds (II) should be used as shown in the above reaction formula.

Although the compound (III) has gelation ability, as shown in the following reaction formula, a thioether moiety is oxidized to be sulfonated so as to obtain the gelling agent of the present invention as a compound (IV).

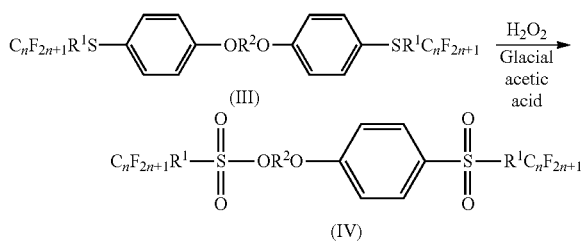

(In the above reaction formula, $R^1$, $R^2$ and n are as defined in the above formula (1).)

The method of using the gelling agent of the present invention is the same as that of a gelling agent of the prior art. For example, after a liquid organic compound to be gelatinized is heated at a temperature equal to or higher than the sol-gel transition temperature to be mixed with and dissolved in the gelling agent uniformly, the resulting solution is left to be cooled to obtain a gel. As a matter of course, one liquid organic compound does not need to be used, and a mixture of several liquid organic compounds or a solution containing a solute dissolved in the liquid organic compound may be used. The liquid organic compound may contain many decomposed components like used food oil, food residue such as tempura residue, or iron mold or mud like waste oil after machine washing.

The gelling agent of the present invention may be used in an amount of 1 to 5 wt % based on the total weight of the gelling agent and the liquid organic compound. There is a case where an amount of about 0.4 wt % which is smaller than 1 wt % suffices. As a matter of course, it may be used in a large amount, for example, 10 wt %. Before use, in consideration of the temperature and strength in a gel state of interest, the optimal compound and its amount should be selected from among the gelling agents of the present invention by carrying out a test on them beforehand, and a person skilled in the art can determine these through an extremely simple preliminary test.

According to the present invention, there is preferably provided a gel which comprises 0.4 to 5 wt % of the gelling agent of the present invention and 99.6 to 95 wt % of an organic compound which is liquid at 25° C.

EXAMPLES

The following examples are provided for the purpose of further illustrating the present invention but are in no way to be taken as limiting.

Synthesis Example 1

Synthesis of Compound A

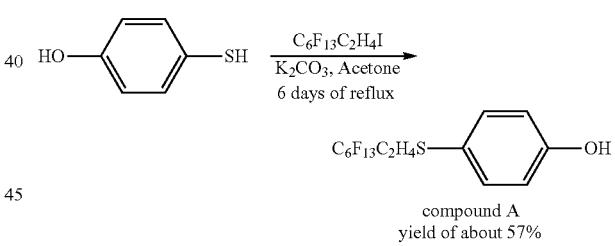

compound A
yield of about 57%

2-(perfluorohexyl)ethyl iodide (25.20 g, 0.0532 moles), 4-hydroxythiophenol (6.74 g, 0.0534 mole), potassium carbonate (8.74 g, 0.632 mole) and acetone (about 100 ml) were fed to a 200 ml eggplant-like flask and refluxed for 6 days. After filtration with a fluted filter, the solvent was evaporated by an evaporator, and the obtained product was recrystallized with chloroform. After filtration with a fluted filter, the solvent was evaporated again by an evaporator. After ethanol was added and dissolved by heating, when water was added and the resulting solution was cooled with iced water, a solid separated out, and suction filtration was carried out.

Figure 1:
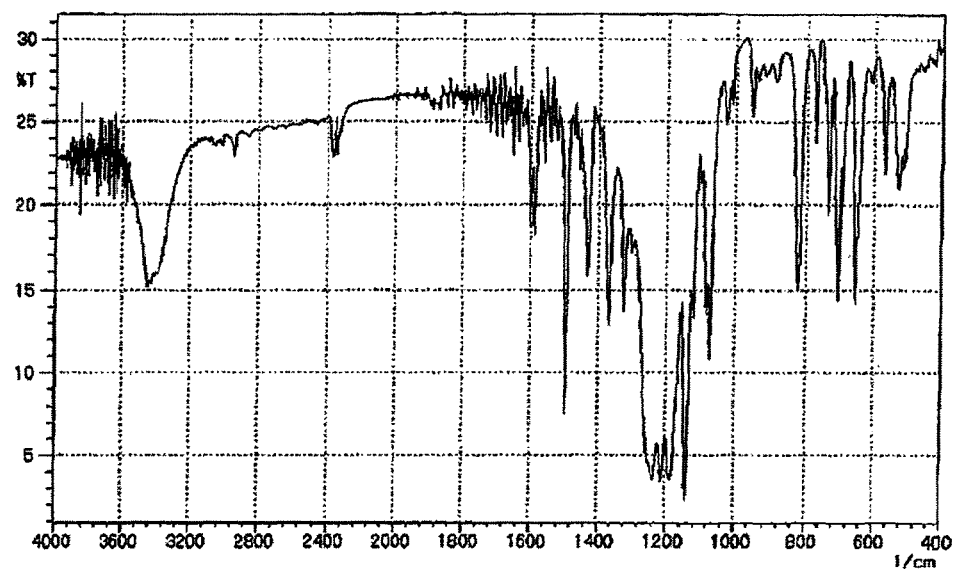
FIG. 1 is an IR spectral diagram of the following compound A which is one of intermediates for producing the gelling agent of the present invention.

Form: white powder
Yield: 14.06 g (56.5%)
Melting point: 63.4 to 68.2° C.
IR (KBr): 1141.9 cm$^{-1}$ (C—O), 1186.2, 1211.3, 1236.4 cm$^{-1}$ (C—F), 3446.8 cm$^{-1}$ (O—H) (see FIG. 1)
$^1$H NMR (CDCl$_3$): δ=2.33 (2H, tt, J=18.8, 8.0 Hz), 2.99 (2H, tt, J=8.0, 4.0 Hz), 3.56 (1H, brs, OH), 6.82 (2H, d, J=8.6 Hz), 7.34 (2H, d, J=8.6 Hz) ppm (see FIG. 8)

Synthesis Example 2

Synthesis of Compound 1-5

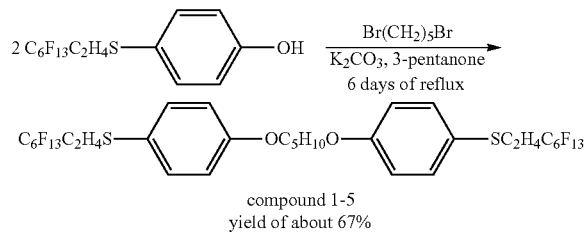

compound 1-5
yield of about 67%

Perfluorophenol (compound A) (5.03 g, 0.0107 mole), 1,5-dibromopentane (1.48 g, 0.00644 mole), potassium carbonate (2.26 g, 0.0164 mole) and 3-pentanone (100 ml) were fed to a 100 ml eggplant-like flask and refluxed for 6 days. Water was added to carry out separation and then brine was added to carry out separation again. After concentration, ethanol was added and heated to dissolve the solid. When the resulting solution was left to be cooled, a white crystal separated out, and suction filtration was carried out.

Form: white powder
Yield: 3.64 g (67.2%)
Melting point: 55 to 57° C.
IR (KBr): 1141.9 cm$^{-1}$ (C—O), 1180.4, 1190.1, 1209.4, 1244.1 cm$^{-1}$ (C—F), 2870.1, 2937.6 cm$^{-1}$ (C—H) (see FIG. 2)
$^1$H NMR (CDCl$_3$): δ=1.67 (2H, quin, J=7.5 Hz), 1.87 (4H, quin, J=7.5 Hz), 2.23-2.43 (4H, m), 2.99 (4H, m), 3.99 (4H, t, J=7.5 Hz), 6.87 (4H, d, J=8.5 Hz), 7.37 (4H, d, J=8.5 Hz) ppm (see FIG. 9)

Synthesis Example 3

Synthesis of Compound 2-5

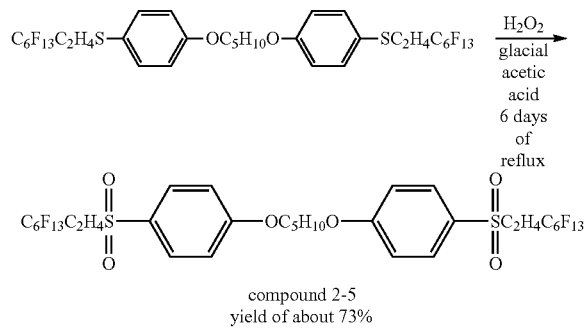

compound 2-5
yield of about 73%

A dimer (3.64 g, 0.00359 mole), H$_2$O$_2$ (0.722 ml, 35%, 0.0212 mole) and glacial acetic acid (15 ml) were fed to a 100 ml eggplant-like flask and stirred in an oil bath at 70° C. for one night. When ether and water were added, a solid separated out. Therefore, a water layer was removed, and then suction filtration was carried out.

When the obtained product was measured by NMR, as the main component of the sample was a dimer sulfide, the same reaction was carried out.

The dimer sulfide (1.04 g, 0.000996 mole), H$_2$O$_2$ (0.198 g, 35%, 0.00582 mole) and glacial acetic acid (5 ml) were fed to a 100 ml eggplant-like flask and stirred in an oil bath at 70° C. for 5 days. When ether and water were added, a solid separated out. Therefore, a water layer was removed, and then suction filtration was carried out. Thereafter, the filtrate was suction filtered with chloroform and concentrated by an evaporator.

Form: white powder
Yield: 0.78 g (72.9%)
Melting point: 154 to 158° C.
IR (KBr): 1147.7 cm$^{-1}$ (C—O), 1188.2, 1230.6, 1267.2 cm$^{-1}$ (C—F), 2866.2, 2941.4 cm$^{-1}$ (C—H) (see FIG. 3)
$^1$H NMR (CDCl$_3$): δ=1.70 (2H, quin, J=7.5 Hz), 1.93 (4H, quin, J=7.5 Hz), 2.48-2.67 (4H, m), 3.28 (4H, m), 4.10 (4H, t, J=7.5 Hz), 7.05 (4H, d, J=8.9 Hz), 7.86 (4H, d, J=8.9 Hz) ppm (see FIG. 10)

Synthesis Example 4

Synthesis of Compound 1-6

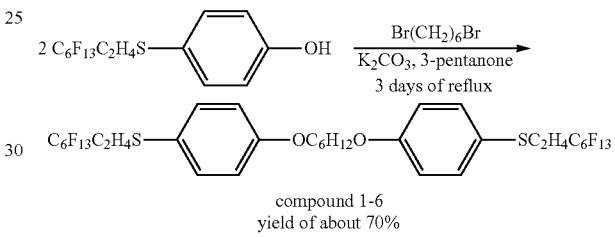

compound 1-6
yield of about 70%

Perfluorophenol (5.06 g, 0.0107 mole), 1,6-dibromohexane (1.33 g, 0.00545 mole), potassium carbonate (2.28 g, 0.0165 mole) and 3-pentanone (50 ml) were fed to a 100 ml eggplant-like flask and refluxed for 3 days. Water was added to carry out separation, and then brine was added to carry out separation again. Since a solid separated out, a turbid water layer was removed, and suction filtration was carried out.

Form: white powder
Yield: 3.94 g (70.4%)
Melting point: 75 to 83° C.
IR (KBr): 1141.9 cm$^{-1}$ (C—O), 1180.4, 1211.3, 1246.0 cm$^{-1}$ (C—F), 2941.4 cm$^{-1}$ (C—H) (see FIG. 4)
$^1$H NMR (CDCl$_3$): δ=1.55 (4H, quin, J=7.0 Hz), 1.82 (4H, quin, J=7.0 Hz), 2.23-2.47 (4H, m), 3.01 (4H, m), 3.97 (4H, t, =7.0 Hz), 6.86 (4H, d, J=8.6 Hz), 7.37 (4H, d, J=8.6 Hz) ppm (see FIG. 11)

Synthesis Example 5

Synthesis of Compound 2-6

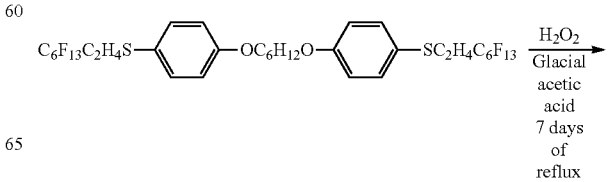

$$C_6F_{13}C_2H_4\overset{O}{\underset{O}{S}}-\underset{}{\bigcirc}-OC_6H_{12}O-\underset{}{\bigcirc}-\overset{O}{\underset{O}{S}}C_2H_4C_6F_{13}$$

compound 2-6
yield of about 15%

A dimer (1.00 g, 0.000974 mole), $H_2O_2$ (0.1 ml, 35%, 0.00288 mole) and glacial acetic acid (5 ml) were fed to a 100 ml eggplant-like flask and stirred in an oil bath at 70° C. for 7 days. When ether and water were added, a solid separated out. Therefore, a water layer was removed, and then suction filtration was carried out. Thereafter, the obtained filtrate was suction filtered with chloroform and concentrated by an evaporator.

Form: white powder
Yield: 0.16 g (15.1%)
Melting point: 143 to 147° C.
IR (KBr): 1139.9, 1151.5 cm$^{-1}$ (C—O), 1193.9, 1211.3, 1234.4, 1253.7 cm$^{-1}$ (C—F), 2939.5 cm$^{-1}$ (C—H) (see FIG. 5)
$^1$H NMR (CDCl$_3$): δ=1.56-1.70 (4H, m), 1.80-1.90 (4H, m), 2.45-2.63 (4H, m), 3.27-3.33 (4H, m), 4.07 (4H, t, =6.5 Hz), 7.04 (4H, d, J=8.9 Hz), 7.85 (4H, d, J=8.9 Hz) ppm (see FIG. 12)

Synthesis Example 6

Synthesis of Compound 1-10

$$2\ C_6F_{13}C_2H_4S-\underset{}{\bigcirc}-OH \xrightarrow[\text{K}_2\text{CO}_3,\ 3\text{-pentanone}]{\text{Br(CH}_2)_{10}\text{Br}} $$
3 days of reflux $$C_6F_{13}C_2H_4S-\underset{}{\bigcirc}-OC_{10}H_{20}O-\underset{}{\bigcirc}-SC_2H_4C_6F_{13}$$

compound 1-10
yield of about 88%

Perfluorophenol (5.03 g, 0.0107 mole), 1,10-dibromodecane (1.61 g, 0.00537 mole), potassium carbonate (2.30 g, 0.0166 mole) and 3-pentanone (50 ml) were fed to a 100 ml eggplant-like flask and refluxed for 3 days. When water was added to carry out separation, a solid separated out. Therefore, a turbid water layer was removed, and suction filtration was carried out.

Form: white powder
Yield: 5.13 g (88.3%)
Melting point: 75.0 to 80.0° C.
IR (KBr): 1141.9 cm$^{-1}$ (C—O), 1180.4, 1192.0, 1211.3, 1246.0 cm$^{-1}$ (C—F), 2850.8, 2918.3, 2939.5 cm$^{-1}$ (C—H) (see FIG. 6)
$^1$H NMR (CDCl$_3$): δ=1.33-1.43 (12H, m), 1.78 (4H, qui, J=6.6 Hz), 2.33 (4H, tt, J=17.3, 8.0 Hz), 2.99 (4H, tt, J=8.0, 4.0 Hz), 3.94 (4H, t, J=6.6 Hz), 6.86 (4H, d, J=8.6 Hz), 7.36 (4H, d, J=8.6 Hz) ppm (see FIG. 13)

Synthesis Example 7

Synthesis of Compound 2-10

$$C_6F_{13}C_2H_4S-\underset{}{\bigcirc}-OC_{10}H_{20}O-\underset{}{\bigcirc}-SC_2H_4C_6F_{13} \xrightarrow[\text{Glacial acetic acid}]{H_2O_2}$$
7 days of reflux $$C_6F_{13}C_2H_4\overset{O}{\underset{O}{S}}-\underset{}{\bigcirc}-OC_{10}H_{20}O-\underset{}{\bigcirc}-\overset{O}{\underset{O}{S}}C_2H_4C_6F_{13}$$

compound 2-10
yield of about 70.7%

A dimer compound 1-10 (2.00 g, 1.85 mmole), $H_2O_2$ (0.9 ml, 35%, 9.3 moles) and glacial acetic acid (10 ml) were fed to a 100 ml eggplant-like flask and stirred in an oil bath at 70° C. for 7 days. When ether and water were added, a solid separated out. Therefore, a water layer was removed, and then suction filtration was carried out. Thereafter, the obtained filtrate was suction filtered with chloroform and concentrated by an evaporator.

Form: white powder
Yield: 1.5 g (70.7%)
Melting point: 156 to 157° C.
IR (KBr): 1211.3 cm$^{-1}$, 1292.3 cm$^{-1}$, 1321.2 cm$^{-1}$, 1599.0, 2918.3 cm$^{-1}$, 2937.6 cm$^{-1}$ (see FIG. 7)
$^1$H NMR (CDCl$_3$): δ=1.25-1.60 (12H, m), 1.79-1.86 (4H, m), 2.56-2.60 (4H, m), 3.27-3.31 (4H, m), 4.04 (4H, t, J—6.5 Hz), 7.04 (4H, d, J=8.9 Hz), 7.84 (4H, d, J=8.9 Hz) ppm (see FIG. 14)
Molecular weight (calculated value): 1146
Experimental value
M/Z=1147 (M+H)

Example 1

Measurement of Minimum Gelation Concentration

The minimum gelation concentration was measured as follows.
[1] The compound is weighed and fed to a sample tube.
[2] Solvents are added.
[3] The compound is dissolved by heating.
[4] The resulting solution is left to be cooled to confirm its gelation at room temperature.
[5] When the solution is gelatinized, the solvents are added again to reduce its concentration.
[6] The steps [3] to [6] are repeated.
The measurement results of the minimum gelation concentration are shown in Table 1.

TABLE 1

| Solvent | Compound 2-5 | Compound 1-6 | Compound 2-6 | Compound 2-10 |
|---|---|---|---|---|
| P13 TFSI | 3.8 | 6.6 | 2.9 | 2.2 |
| PC | 3.0 | 6.3 | 4.2 | 4.3 |

TABLE 1-continued

| Solvent | Compound 2-5 | Compound 1-6 | Compound 2-6 | Compound 2-10 |
|---|---|---|---|---|
| GBL | 3.7 | 8.6 | 5.0 | 5.7 |
| 1-octanol | 4.6 | 7.2 | 7.1 | 2.9 |
| ethanol | 5.7 | 9.5 | 8.0 | 7.3 |
| acetonitrile | 5.2 | 5.7 | 7.2 | 9.0 |
| DMC | 8.6 | 8.5 | — | 7.1 |

The minimum additional amount (wt %) for gelation at room temperature
P13TFSI: N-methyl-N-propylpyrrolidinium bis(trifluoromethanesulfonyl)imide
PC: propylene carbonate
GBL: γ-butyrolactone
DMC: dimethyl carbonate The minimum gelation concentrations of the compounds 2-5, 2-6 and 2-10 in organic solvents are shown in Table 1. (reference example in the case of compound 1-6)

As the value becomes smaller, an organic gel is formed by adding a smaller amount of the compound. That is, the compound has higher gelation ability.

The minimum gelation concentration is very low in solvents such as P13 TFSI, PC and GBL, which makes it clear that gelation ability increases as the carbon chain becomes longer. Meanwhile, when sulfonated compounds 2-5, 2-6 and 2-10 are compared with one another, regardless of the number of carbon atoms at the center, the minimum gelation concentrations of these sulfonated compounds become almost the same value. When the compound 1-6 is compared with the compound 2-6, it is seen that the sulfonated compound 2-6 has higher gelation ability.

Example 2

Measurement of Sol-Gel Transition Temperature

The measurement of the sol-gel transition temperature was carried out as follows.
[1] The compound is weighed and fed to a sample tube.
[2] Solvents are added to adjust the concentration to around 10 wt %.
[3] The compound is dissolved by heating.
[4] The resulting solution is left to be cooled so as to be gelatinized at room temperature.
[5] The gel is heated with a ribbon heater to check a temperature at which the gel changes into sol.
[6] The solvent is added again to reduce the concentration gradually and check a temperature at which the gel becomes sol.

The compounds 2-5, 2-6 and 2-10 were measured in P13 TFSI, PC, GBL and 1-octanol solvents.

The sol-gel transition temperatures of the compound 2-5 in PC and GBL rarely changed with respect to the concentration but drastically changed when 5 wt % of P13 TFSI and 7 wt % of 1-octanol were used.

Although the sol-gel transition temperatures of the compound 2-6 in P13 TFSI, PC and GBL were almost the same at 6 wt % or more, the sol-gel transition temperature of the compound 2-6 in 1-octanol was lower than those in other solvents.

The sol-gel transition temperature of the compound 2-10 in P13 TFSI was the highest.

The results are shown in the graphs of FIGS. 15 to 17.

Example 3

Gelation Examples of Various Oils

The gelatinized states of salad oil, silicon oil manufactured by Toshiba Silicone Co., Ltd. (TSF483) (methyl hydrogen polysiloxane-dimethylpolysiloxane copolymer) and Neoback MR-200 (registered) oil manufactured by Matsumura Sekiyu Co., Ltd. (physical values: ISO viscosity grade of 68, density of 0.883 g/cm$^3$ (15° C.)) are shown in Tables 2 to 4 (in Tables 2 to 4, "%" means "wt %").

TABLE 2

Salad Oil

| Compound 2-10 | | Compound 2-5 | |
|---|---|---|---|
| Gelling agent % | Sol-gel transition temperature (° C.) | Gelling agent % | Sol-gel transition temperature (° C.) |
| 5.4 | 50.6 | 5.9 | 63.6 |
| 4.7 | 50.0 | 4.7 | 58.1 |
| 3.4 | 49.2 | 3.4 | 58.5 |
| 3.1 | 49.1 | 2.6 | 58.6 |
| 2.9 | Not gelatinized | 2.3 | Not gelatinized |

TABLE 3

Silicon oil
Compound 2-10

| Gelling agent % | Sol-gel transition temperature (° C.) |
|---|---|
| 5.0 | 56.7 |
| 4.2 | 55.0 |
| 3.3 | 54.3 |
| 2.2 | 54.0 |
| 1.8 | Not gelatinized |

TABLE 4

Neoback MR-200

| Compound 2-10 | | Compound 2-5 | |
|---|---|---|---|
| Gelling agent % | Sol-gel transition temperature (° C.) | Gelling agent % | Sol-gel transition temperature (° C.) |
| 5.0 | 53.4 | 5.6 | 74.4 |
| 4.4 | 52.1 | 5.0 | 72.4 |
| 3.8 | 49.3 | 4.3 | 72.1 |
| 3.7 | 47.6 | 3.7 | 71.9 |
| 3.5 | Not gelatinized | 3.2 | Not gelatinized |

EFFECT OF THE INVENTION

The present invention is a gelling agent which comprises a novel compound represented by the above formula (1), and the gelling agent of the present invention can gelatinize or thicken various organic compounds which are liquid at room temperature, such as hydrocarbons, alcohols, ketones, esters, carboxylic acids, amines, nitriles and amides.

As shown in the above examples, the gelling agent of the present invention can gelatinize an organic compound at room temperature with not more than 1 wt % by selecting an organic compound to be used in combination therewith or can keep a gel at a temperature of around 80° C. by selecting a certain combination. Therefore, it is a gelling agent which is extremely industrially useful.

INDUSTRIAL APPLICABILITY

The gelling agent of the present invention can be used to control fluidity and provide thixotropy in the fields of adhesives, coating compositions, printing inks and cosmetics, to collect oil when it outflows into the sea, to dispose of waste food oil for domestic use, and to solidify and thicken liquid organic compounds in the medical field and various industrial fields.

The invention claimed is:

1. A gelling agent comprising a compound represented by the following formula (1):

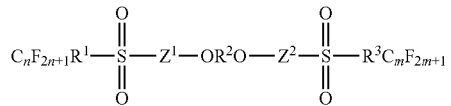

wherein n and m are each independently an integer of 2 to 18, $R^1$ and $R^3$ are each independently a single bond or a branched or linear alkylene group having 1 to 6 carbon atoms, $R^2$ is a branched or linear alkylene group having 3 to 18 carbon atoms, and $Z^1$ and $Z^2$ are each independently a phenylene group or a biphenylene group.

2. A gel comprising 0.4 to 5 wt % of the gelling agent of claim 1 and 99.6 to 95 wt % of an organic compound which is liquid at 25° C.

* * * * *